US008049519B2

(12) United States Patent
Nielsen et al.

(10) Patent No.: US 8,049,519 B2
(45) Date of Patent: Nov. 1, 2011

(54) CONTACT FREE ABSOLUTE POSITION DETERMINATION OF A MOVING ELEMENT IN A MEDICATION DELIVERY DEVICE (75) Inventors: Preben Nielsen, Holbæk (DK); Bodo Von Münchow, Lyngby (DK)

(73) Assignee: Novo Nordisk A/S, Bagsvaerd (DK)

( * ) Notice: Subject to any disclaimer, the term of this patent is extended or adjusted under 35 U.S.C. 154(b) by 600 days.

(21) Appl. No.: 12/298,330

(22) PCT Filed: Apr. 25, 2007

(86) PCT No.: PCT/EP2007/054069
§ 371 (c)(1),
(2), (4) Date: Nov. 11, 2008

(87) PCT Pub. No.: WO2007/122253
PCT Pub. Date: Nov. 1, 2007

(65) Prior Publication Data
US 2009/0096467 A1 Apr. 16, 2009

(30) Foreign Application Priority Data

Apr. 26, 2006 (EP) ..................................... 06008597

(51) Int. Cl.
*G01R 27/26* (2006.01)
*A61B 18/18* (2006.01)
(52) U.S. Cl. .......................................... 324/662; 606/41
(58) Field of Classification Search .................... 324/662
See application file for complete search history.

(56) References Cited

U.S. PATENT DOCUMENTS 3,700,862 A  10/1972  Snook et al.
3,809,863 A   5/1974  Oberg
3,916,157 A  10/1975  Roulette et al.
3,998,513 A  12/1976  Kobayashi et al.
4,179,212 A  12/1979  Lahr
(Continued)

FOREIGN PATENT DOCUMENTS
CN       1051152       1/1997
(Continued)

OTHER PUBLICATIONS

English Language Abstract of JP 09-034361.
English Language Abstract of DE 3712089.
English Language Abstract of JP 2001-075480.
English Language Abstract of JP 2002-082120.
English Language Abstract of JP 2001-043301.
English Language Abstract of JP 2000-272191 (provided by EPO).

(Continued)

*Primary Examiner* — Jeff Natalini
(74) *Attorney, Agent, or Firm* — Wesley A. Nicolas; Marc A. Began (57) ABSTRACT

The present invention relates to a medication delivery device for expelling set doses of medicament, the medication delivery device comprising a position determining assembly for detecting absolute positions of a rotatably mounted member arranged within the device, the position determining assembly comprising a plurality of transmitter electrodes arranged on a first exterior surface part of the rotatably mounted member, a plurality of receiver electrodes arranged on a second exterior surface part of the rotatably mounted member. A number of transmitter electrodes form pairs of interconnected electrodes with a number of receiver electrodes. A reading assembly fixedly arranged relative to for example the housing of the medication delivery device is also provided. The reading assembly comprises a plurality of transmitters arranged to electrically couple to one or more receiver electrodes, the reading assembly further comprising a plurality of receivers arranged to electrically couple to one or more transmitter electrodes.

25 Claims, 6 Drawing Sheets a)

b)

U.S. PATENT DOCUMENTS

| | | |
|---|---|---|
| 4,327,283 A | 4/1982 | Henman et al. |
| 4,355,300 A | 10/1982 | Weber |
| 4,420,754 A | 12/1983 | Andermo |
| 4,449,042 A | 5/1984 | Hampson et al. |
| 4,476,149 A | 10/1984 | Poppe et al. |
| 4,476,381 A | 10/1984 | Rubin |
| 4,591,707 A | 5/1986 | Stenzel et al. |
| 4,625,101 A | 11/1986 | Hinks et al. |
| 4,636,786 A | 1/1987 | Haertling |
| 4,693,574 A | 9/1987 | Ohnuki et al. |
| 4,731,526 A | 3/1988 | Knoll et al. |
| 4,739,377 A | 4/1988 | Allen |
| 4,810,867 A | 3/1989 | Speicher |
| 4,850,966 A | 7/1989 | Grau et al. |
| 4,853,521 A | 8/1989 | Claeys et al. |
| 4,857,716 A | 8/1989 | Gombrich et al. |
| 4,880,014 A | 11/1989 | Zarowitz et al. |
| 4,896,946 A | 1/1990 | Suzuki et al. |
| 4,930,263 A | 6/1990 | Rando |
| 4,950,246 A | 8/1990 | Muller |
| 4,959,056 A | 9/1990 | Dombrowski et al. |
| 4,978,335 A | 12/1990 | Arthur |
| 5,053,715 A * | 10/1991 | Andermo ............... 324/662 |
| 5,059,776 A | 10/1991 | Antes |
| 5,077,635 A * | 12/1991 | Bollhagen et al. ......... 361/287 |
| 5,078,683 A | 1/1992 | Sancoff et al. |
| 5,091,798 A | 2/1992 | Hibino |
| 5,132,026 A | 7/1992 | Baluyet et al. |
| 5,153,827 A | 10/1992 | Courte et al. |
| 5,174,766 A | 12/1992 | Yoshizawa et al. |
| 5,176,502 A | 1/1993 | Sanderson et al. |
| 5,196,683 A | 3/1993 | Marom et al. |
| 5,271,527 A | 12/1993 | Haber et al. |
| 5,305,147 A | 4/1994 | Hasegawa et al. |
| 5,311,364 A | 5/1994 | Kanoshima et al. |
| 5,317,506 A | 5/1994 | Coutre et al. |
| 5,336,871 A | 8/1994 | Colgate, Jr. |
| 5,379,131 A | 1/1995 | Yamazaki |
| 5,394,206 A | 2/1995 | Cocca |
| 5,403,616 A | 4/1995 | Hattori et al. |
| 5,418,649 A | 5/1995 | Igarashi |
| 5,422,472 A | 6/1995 | Tavislan et al. |
| 5,430,278 A | 7/1995 | Krieg et al. |
| 5,432,329 A | 7/1995 | O'Boyle et al. |
| 5,461,239 A | 10/1995 | Atherton |
| 5,523,560 A | 6/1996 | Manique et al. |
| 5,569,212 A | 10/1996 | Brown |
| 5,585,615 A | 12/1996 | Iwanami et al. |
| 5,593,390 A | 1/1997 | Castellano et al. |
| 5,628,309 A | 5/1997 | Brown |
| 5,637,854 A | 6/1997 | Thomas |
| 5,643,212 A | 7/1997 | Coutre et al. |
| 5,675,380 A | 10/1997 | Florent |
| 5,686,725 A | 11/1997 | Maruyama et al. |
| 5,747,350 A | 5/1998 | Sattler |
| 5,757,521 A | 5/1998 | Walters et al. |
| 5,764,457 A | 6/1998 | Uhde et al. |
| 5,777,303 A | 7/1998 | Berney |
| 5,782,814 A | 7/1998 | Brown et al. |
| 5,786,584 A | 7/1998 | Button et al. |
| 5,791,880 A | 8/1998 | Wilson |
| 5,792,117 A | 8/1998 | Brown |
| 5,793,502 A | 8/1998 | Bianco |
| 5,821,521 A | 10/1998 | Bridgelall et al. |
| 5,821,524 A | 10/1998 | Horlbeck |
| 5,876,380 A | 3/1999 | Manganini et al. |
| 5,880,683 A | 3/1999 | Brandestini |
| 5,882,463 A | 3/1999 | Tompkin et al. |
| 5,895,369 A | 4/1999 | Flower |
| 5,902,990 A | 5/1999 | Stewart |
| 5,920,198 A * | 7/1999 | Suzuki et al. .......... 324/662 |
| 5,925,867 A | 7/1999 | Hagimoto |
| 5,954,700 A | 9/1999 | Kovelman |
| 5,986,585 A | 11/1999 | Pusch |
| 6,003,775 A | 12/1999 | Ackley |
| 6,019,745 A | 2/2000 | Gray |
| 6,047,892 A | 4/2000 | Schuessler et al. |
| 6,053,415 A | 4/2000 | Norwood |
| 6,068,615 A | 5/2000 | Brown et al. |
| 6,090,064 A | 7/2000 | Reilly et al. |
| 6,110,148 A | 8/2000 | Brown et al. |
| 6,110,152 A | 8/2000 | Kovelman |
| 6,168,080 B1 | 1/2001 | Verschuur et al. |
| 6,177,683 B1 | 1/2001 | Kolesar et al. |
| 6,202,929 B1 | 3/2001 | Verschuur et al. |
| 6,215,508 B1 | 4/2001 | Bryan et al. |
| 6,265,466 B1 | 7/2001 | Glatkowski et al. |
| 6,274,092 B1 | 8/2001 | Itoh |
| 6,329,813 B1 | 12/2001 | Andermo |
| 6,352,523 B1 | 3/2002 | Brown et al. |
| 6,372,293 B1 | 4/2002 | Mathus et al. |
| 6,435,175 B1 | 8/2002 | Stenzler |
| 6,475,192 B1 | 11/2002 | Reilly et al. |
| 6,533,183 B2 | 3/2003 | Aasmul et al. |
| 6,598,796 B2 | 7/2003 | Harrop |
| 6,652,812 B1 | 11/2003 | Vartiainen et al. |
| 6,669,090 B2 | 12/2003 | Eilersen |
| 6,700,391 B2 | 3/2004 | Strack et al. |
| 6,813,868 B2 | 11/2004 | Baldwin et al. |
| 6,854,653 B2 | 2/2005 | Eilersen |
| 6,876,209 B2 * | 4/2005 | Lin et al. ................ 324/660 |
| 6,954,700 B2 | 10/2005 | Higashida et al. |
| 6,957,522 B2 | 10/2005 | Baldwin et al. |
| 6,976,349 B2 | 12/2005 | Baldwin et al. |
| 6,994,261 B2 | 2/2006 | Eilersen |
| 7,018,363 B2 | 3/2006 | Cowan et al. |
| 7,041,941 B2 | 5/2006 | Faries et al. |
| 7,061,831 B2 | 6/2006 | De La Huerga |
| 7,077,332 B2 | 7/2006 | Verschuur et al. |
| 7,104,973 B2 | 9/2006 | Woolston et al. |
| 7,108,184 B2 | 9/2006 | Mase et al. |
| 7,138,806 B2 * | 11/2006 | Gafner et al. ............... 324/660 |
| 2001/0001472 A1 | 5/2001 | Sano et al. |
| 2001/0013544 A1 | 8/2001 | Rathus et al. |
| 2001/0015202 A1 | 8/2001 | Miller |
| 2001/0034506 A1 | 10/2001 | Hirschman et al. |
| 2002/0000471 A1 | 1/2002 | Aasmul et al. |
| 2002/0012176 A1 | 1/2002 | Ning |
| 2002/0020654 A1 | 2/2002 | Eilersen |
| 2002/0022821 A1 | 2/2002 | Eilersen |
| 2002/0063156 A1 | 5/2002 | Marchand |
| 2002/0106309 A1 | 8/2002 | Mathus et al. |
| 2002/0117549 A1 | 8/2002 | Lee |
| 2002/0117579 A1 | 8/2002 | Kotoulas et al. |
| 2002/0123078 A1 | 9/2002 | Seul et al. |
| 2003/0015590 A1 | 1/2003 | Chen |
| 2003/0039590 A1 | 2/2003 | Lodge |
| 2003/0116630 A1 | 6/2003 | Carey et al. |
| 2003/0143614 A1 | 7/2003 | Drmanac |
| 2003/0205625 A1 | 11/2003 | Eilersen |
| 2003/0233069 A1 | 12/2003 | Gillespie et al. |
| 2004/0008853 A1 | 1/2004 | Pelrine et al. |
| 2004/0024368 A1 | 2/2004 | Broselow |
| 2004/0046032 A1 | 3/2004 | Urano et al. |
| 2004/0051368 A1 | 3/2004 | Caputo et al. |
| 2004/0141426 A1 | 7/2004 | Kawasaki et al. |
| 2004/0155113 A1 | 8/2004 | Urano et al. |
| 2004/0178255 A1 | 9/2004 | Eich et al. |
| 2004/0200558 A1 | 10/2004 | Stevens et al. |
| 2004/0207385 A1 | 10/2004 | Gafner et al. |
| 2004/0210199 A1 | 10/2004 | Atterbury et al. |
| 2005/0006472 A1 | 1/2005 | Verschuur et al. |
| 2005/0035207 A1 | 2/2005 | Philyaw et al. |
| 2005/0060059 A1 | 3/2005 | Klein et al. |
| 2005/0116033 A1 | 6/2005 | Moore |
| 2005/0156318 A1 | 7/2005 | Douglas |
| 2005/0182360 A1 | 8/2005 | Yeandel et al. |
| 2005/0236603 A1 | 10/2005 | Faris |
| 2005/0283116 A1 | 12/2005 | Eakins et al. |
| 2006/0097877 A1 | 5/2006 | Baba et al. |
| 2006/0118612 A1 | 6/2006 | Christoffersen et al. |
| 2006/0125491 A1 | 6/2006 | Grishin et al. |
| 2006/0129104 A1 | 6/2006 | Cowan et al. |
| 2006/0138233 A1 | 6/2006 | Kemppainen et al. |
| 2006/0164002 A1 | 7/2006 | O'Brien et al. |
| 2006/0170981 A1 | 8/2006 | Ricks et al. |
| 2006/0175427 A1 | 8/2006 | Jonientz et al. |

| | | | |
|---|---|---|---|
| 2006/0176267 A1 | 8/2006 | Honeyman et al. | |
| 2006/0224123 A1 | 10/2006 | Friedli et al. | |
| 2006/0226238 A1 | 10/2006 | Salib et al. | |
| 2006/0243804 A1 | 11/2006 | Christoffersen et al. | |
| 2007/0080234 A1 | 4/2007 | Demoy | |
| 2007/0239116 A1 | 10/2007 | Follman et al. | |
| 2008/0015510 A1 | 1/2008 | Sandoz et al. | |
| 2009/0088701 A1 | 4/2009 | Larsen | |

FOREIGN PATENT DOCUMENTS

| | | |
|---|---|---|
| DE | 1950411 | 11/1966 |
| DE | 2636634 | 2/1978 |
| DE | 3712089 | 10/1988 |
| DE | 4234016 | 4/1993 |
| DE | 4402319 | 8/1994 |
| DE | 19504111 | 8/1995 |
| DE | 19637967 | 10/1997 |
| DE | 19814687 | 2/1999 |
| DE | 10035192 | 10/2001 |
| EP | 0235691 | 2/1987 |
| EP | 248165 | 12/1987 |
| EP | 0248165 A2 | 12/1987 |
| EP | 398717 | 11/1990 |
| EP | 402553 | 12/1990 |
| EP | 0364010 | 4/1993 |
| EP | 626660 | 11/1994 |
| EP | 685810 | 12/1994 |
| EP | 0690457 | 5/1995 |
| EP | 0336778 | 12/1995 |
| EP | 716290 | 6/1996 |
| EP | 0492954 | 10/1996 |
| EP | 833273 | 4/1998 |
| EP | 0833278 | 4/1998 |
| EP | 0573129 | 8/1998 |
| EP | 0911859 | 10/1998 |
| EP | 0588427 | 11/1998 |
| EP | 1142643 | 10/2001 |
| EP | 1143643 | 10/2001 |
| EP | 1246127 | 3/2002 |
| EP | 1193641 | 4/2002 |
| EP | 1462134 | 9/2004 |
| EP | 1503185 | 2/2005 |
| FR | 2771111 | 5/1999 |
| GB | 2088163 | 6/1982 |
| GB | 2159007 | 11/1985 |
| GB | 2216259 | 10/1989 |
| GB | 2287551 | 9/1995 |
| GB | 2309801 | 8/1997 |
| GB | 2336927 | 11/1999 |
| GB | 2341965 | 3/2000 |
| JP | 56-094475 | 7/1981 |
| JP | 59-131917 A | 7/1984 |
| JP | 63-100303 A | 5/1988 |
| JP | 285370 | 3/1990 |
| JP | 2-188702 | 7/1990 |
| JP | 2-250083 | 10/1990 |
| JP | 3-27037 A | 2/1991 |
| JP | 4-222084 A | 8/1992 |
| JP | 4-233680 A | 8/1992 |
| JP | 4-233684 A | 8/1992 |
| JP | 5006449 | 1/1993 |
| JP | 5-500917 | 2/1993 |
| JP | 05-314296 | 11/1993 |
| JP | 6-163027 | 6/1994 |
| JP | 06-171194 | 6/1994 |
| JP | 6-333102 | 12/1994 |
| JP | 7-098752 | 4/1995 |
| JP | 07-271890 | 10/1995 |
| JP | 8-106648 | 4/1996 |
| JP | 8-118864 | 5/1996 |
| JP | 8-179475 | 7/1996 |
| JP | 8220994 | 8/1996 |
| JP | 8-262980 | 10/1996 |
| JP | 9-16703 | 1/1997 |
| JP | 09-034361 | 2/1997 |
| JP | 9-91364 | 4/1997 |
| JP | 9-192220 | 7/1997 |
| JP | 09-223181 | 8/1997 |
| JP | 09-274637 | 10/1997 |
| JP | 10-105635 | 4/1998 |
| JP | 10-268777 | 10/1998 |
| JP | 11-135172 | 5/1999 |
| JP | 11-162591 | 6/1999 |
| JP | 11-180079 | 7/1999 |
| JP | 11-276583 | 10/1999 |
| JP | 11-316877 | 11/1999 |
| JP | 2000-040119 | 2/2000 |
| JP | 2000-272191 | 3/2000 |
| JP | 2001-043301 | 2/2001 |
| JP | 2001-075480 | 3/2001 |
| JP | 2002-082120 | 3/2002 |
| JP | 2002-517737 | 6/2002 |
| JP | 4-233624 B2 | 12/2008 |
| WO | WO 91/04759 | 4/1991 |
| WO | WO 92/17231 | 10/1992 |
| WO | WO 93/12828 | 7/1993 |
| WO | WO 94/08647 | 4/1994 |
| WO | WO 94/12235 | 6/1994 |
| WO | 94/15120 | 7/1994 |
| WO | WO 95/28190 | 10/1995 |
| WO | WO 99/60533 | 11/1999 |
| WO | WO 99/65548 | 12/1999 |
| WO | WO 00/42678 | 1/2000 |
| WO | WO 01/22348 | 3/2001 |
| WO | WO 01/54055 | 7/2001 |
| WO | WO 01/62322 | 8/2001 |
| WO | WO 01/70304 | 9/2001 |
| WO | WO 01/84542 | 11/2001 |
| WO | 0195959 | 12/2001 |
| WO | WO 02/11792 | 2/2002 |
| WO | WO 02/13133 | 2/2002 |
| WO | WO 02/092153 | 11/2002 |
| WO | WO 02/095675 | 11/2002 |
| WO | WO 03/017915 | 3/2003 |
| WO | WO 03-020598 | 3/2003 |
| WO | WO 03/038738 | 5/2003 |
| WO | WO 2004/084795 | 10/2004 |
| WO | WO 2004/097715 | 11/2004 |
| WO | WO 2005/075010 | 8/2005 |
| WO | WO 2005/089835 | 9/2005 |
| WO | 2005/110387 | 11/2005 |
| WO | 2006/113521 | 10/2006 |
| WO | 2006/120182 | 11/2006 |
| WO | WO 2007/039148 A1 | 4/2007 |
| WO | WO 2007/107562 | 9/2007 |
| WO | WO 2007/116090 A1 | 10/2007 |
| WO | WO 2007/122253 | 11/2007 |
| WO | WO 2009/015933 | 2/2009 |

OTHER PUBLICATIONS

English Language Abstract of JP 05-314296.
English Language Abstract of JP07-271890.
English Language Abstract of JP 09-223181.
English Language Abstract of JP 09-274637.
English Language Abstract of JP 11-316877.
English Language Abstract of WO 0122348.
Office Action dated Jan. 4, 2008 from U.S. Appl. No. 11/396,889, an application filed Apr. 3, 2006 by Christoffersen et al.
International Search Report for PCT/EP2006/009240, mailed Jan. 4, 2007.
International Search Report for PCT/EP2007/053558, mailed Jul. 23, 2007.
English Abstract of CN1051152.
Japanese Office Action in Related Case Japanese Application No. 2002-518416 Filed Feb. 10, 2003.
JP 11-276583 English Abstract Oct. 12, 1999.
JP 06-171194 English Abstract Jun. 21, 1994.
JP 56-094475 English Abstract Jul. 30, 1981.
JP 5006449 English Abstract Jan. 14, 1993.
Non-Final Office Action Mailed Oct. 30, 2010 in U.S. Appl. No. 11/912,347, filed Oct. 23, 2007; First Named Inventor: Preben Mikael Nielsen.
Final Office Action Mailed Apr. 15, 2011 in U.S. Appl. No. 11/912,347, filed Oct. 23, 2007; First Named Inventor: Preben Mikael Nielsen.

Non-Final Office Action Mailed Sep. 29, 2010 in U.S. Appl. No. 12/293,251, filed Sep. 16, 2008; First Named Inventor: Andre Larsen.
Final Office Action Mailed Apr. 14, 2011 in U.S. Appl. No. 12/293,251, filed Sep. 16, 2008; First Named Inventor: Andre Larsen.
International Search Report for PCT/EP07/054069, mailed Sep. 17, 2007.
CN 1013704 English Abstract, Aug. 28, 1991, CN1013704 previously cited.
DE 19814687 Machine Translation, Feb. 18, 1999.
DE 19637967 English Abstract, Oct. 30, 1997.
DE 19504111 Machine Translation, Aug. 10, 1995, DE 19504111 previously cited.
DE 10035192 Machine Translation, Oct. 11, 2001.
DE 4402319 English Abstract, published Aug. 4, 1994.
DE 4234016 English Abstract, Apr. 15, 1993.
DE 2636634 English Abstract, Feb. 16, 1978.
FR 2771111 Machine Translation, May 21, 1999.
JP 2002-517737 Machine Translation, Jun. 18, 2002.
JP 2000-040119 Machine Translation, Feb. 8, 2000.
JP 11-180079 Machine Translation, Jul. 6, 1999.
JP 11-162591 Machine Translation, Jun. 18, 1999.
JP 11-135172 Machine Translation, May 21, 1999.
JP 10-268777 Machine Translation, Oct. 9, 1998.
JP 10-105635 Machine Translation, Apr. 24, 1998.
JP 9-192220 Machine Translation, Jul. 29, 1997.
JP 9-091364 Machine Translation, Apr. 4, 1997, JP 9-091364 previously cited.
JP 8-262980 Machine Translation, Oct. 11, 1996.
JP 9-16703 Machine Translation, Jan. 17, 1997.
JP 8-220994 Machine Translation, Aug. 30, 1996.
JP 8-179475 Machine Translation, Jul. 12, 1996.
JP 8-118864 Machine Translation, May 14, 1996.
JP 8-106648 Machine Translation, Apr. 23, 1996.
JP 7-098752 Machine Translation, Apr. 11, 1995.
JP 6-333102 Machine Translation, Dec. 2, 1994.
JP 63-100303 English Abstract, May 2, 1988.
JP 6-163027 Machine Translation, Jun. 10, 1994.
JP 59-131917 English Abstract, Jul. 28, 1984.
JP 5-500917 English Abstract, Feb. 25, 1993.
JP 4-233684 English Abstract, Aug. 21, 1992.
JP 4-233680A English Abstract, Aug. 21, 1992.
JP 4-233624B2 Machine Translation, Dec. 19, 2008.
JP 4-222084 English Abstract, Aug. 12, 1992.
JP 327037 Machine Translation.
JP 2-250083 English Abstract, Oct. 5, 1990.
JP 2-188702 English Abstract, Jul. 24, 1990.
JP 285370 Machine Translation.
Notice of Allowance mailed Sep. 17, 2009 in U.S. Appl. No. 11/296,991, filed Dec. 8, 2005 by Eilersen et al.
Notice of Allowance mailed Apr. 30, 2009 in U.S. Appl. No. 11/296,991, filed Dec. 8, 2005 by Eilersen et al.
Non-Final Office Action mailed Oct. 14, 2008 in U.S. Appl. No. 11/296,991, filed Dec. 8, 2005 by Eilersen et al.
Corrected Notice of Allowance mailed Jun. 19, 2009 in U.S. Appl. No. 11/232,469, filed Sep. 19, 2005 by Christoffersen et al.
Notice of Allowance mailed Jun. 8, 2009 in U.S. Appl. No. 11/232,469, filed Sep. 19, 2005 by Christoffersen et al.
Non-Final Office Action mailed Dec. 17, 2008 in U.S. Appl. No. 11/232,469, filed Sep. 19, 2005 by Christoffersen et al.
Final Office Action mailed Jul. 2, 2008 in U.S. Appl. No. 11/232,469, filed Sep. 19, 2005 by Christoffersen et al.
Non-Final Office Action mailed Jan. 3, 2008 in U.S. Appl. No. 11/232,469, filed Sep. 19, 2005 by Christoffersen et al.
Non-Final Office Action mailed Jun. 19, 2007 in U.S. Appl. No. 11/232,469, filed Sep. 19, 2005 by Christoffersen et al.
Non-Final Office Action mailed Oct. 23, 2003 in U.S. Appl. No. 10/463,915, filed Jun. 18, 2003 by Eilersen et al.
Non-Final Office Action mailed Apr. 15, 2004 in U.S. Appl. No. 10/463,915, filed Jun. 18, 2003 by Eilersen et al.
Notice of Allowance mailed Aug. 16, 2004 in U.S. Appl. No. 10/463,915, filed Jun. 18, 2003 by Eilersen et al.
Notice of Allowance mailed Aug. 11, 2005 in U.S. Appl. No. 09/925,792, filed Aug. 9, 2001 by Eilersen et al.
Non-Final Office Action mailed Apr. 4, 2005 in U.S. Appl. No. 09/925,792, filed Aug. 9, 2001 by Eilersen et al.

* cited by examiner

CONTACT FREE ABSOLUTE POSITION DETERMINATION OF A MOVING ELEMENT IN A MEDICATION DELIVERY DEVICE

CROSS-REFERENCE TO RELATED APPLICATIONS

This application is a 35 U.S.C. §371 national stage application of International Patent Application PCT/EP2007/054069 (published as WO 2007/122253), filed Apr. 25, 2007, which claimed priority of European Patent Application 06008597.4, filed Apr. 26, 2006; this application further claims priority under 35 U.S.C. §119 of U.S. Provisional Application 60/797,445, filed May 3, 2006.

FIELD OF THE INVENTION

The present invention relates to an assembly and a method for determining an absolute position of a first member, such as a rotatably mounted dose indication barrel, in a medication delivery device. In particular, the present invention relates to an assembly which takes up a minimum amount of space.

BACKGROUND OF THE INVENTION

U.S. Pat. No. 4,420,754 discloses a system for measuring the relative movement between two elements, such as the scale and slide of a hand-held measuring instrument. The system includes the provision of a number of groups of supply electrodes on the slide, each of the electrodes in each group being supplied from a respective one of a multiple number of output signals from a signal generator so that all of the supply electrodes are furnished with voltages according to a cyclic pattern, the slide also having at least one receiving electrode which feeds a signal processing unit. The scale is provided with an electronic pattern comprising internally galvanically connected parts, one being a detecting part, located close to the area where the supply electrodes of the slide are moved, the other of the two parts being a transferring part which is located close to the area where the receiving electrode of the slide is moved. The movement of the slide along the scale generates a signal from the receiving electrode which is derived from the signals from at least two adjacent supply electrodes and the position of the slide is determined by a signal processing unit which identifies the amplitude ratio of the received signals.

U.S. Pat. No. 6,329,813 discloses an inductive absolute position sensor applying at least one magnetic field generator that generates a first changing magnetic flux in a first flux region. A plurality of coupling loops have a first plurality of coupling loop portions spaced at an interval related to a first wavelength along a measuring axis and a second plurality of coupling loop portions spaced at an interval related to a second wavelength along a measuring axis. One of the first plurality of coupling loop portions and the second plurality of coupling loop portions are inductively coupled to a first changing magnetic flux from a transmitter winding in a first flux region to generate a second changing magnetic flux outside the first flux region in the other of the first plurality of coupling loop portions and the second plurality of coupling loop portions. A magnetic flux sensor is positioned outside the first flux region and is responsive to the second changing magnetic flux to generate a position-dependent output signal. The output signal varies at the first or second wavelength of the corresponding other of the first plurality of coupling loop portions and the second plurality of coupling loop portions that generates the second changing magnetic flux.

The arrangements suggested in both U.S. Pat. Nos. 4,420,754 and 6,329,813 are adapted for determining linear translations between two objects.

US 2004/0207385 relates to a device for detecting the position of a rotor relative to a stator, wherein at least one electrode is arranged on the rotor and at least one electrode is arranged on the stator, such that the electrodes at least partially overlap in at least one rotational position of the rotor relative to the stator. US 2004/0207385 further relates to a method for measuring the rotational position of a rotor comprising at least one rotor electrode relative to a stator comprising at least one stator electrode, wherein the rotational position is detected using a capacitive coupling between the rotor electrode and the stator electrode.

US 2004/0207385 relates to the determining of angular positions between two objects such as between a rotatably mounted rotor and a stationary stator. It is a disadvantage of the arrangement suggested in US 2004/0207385 that the emitters and receivers are position in a manner where they take up an unnecessary amount of space. For compact systems the solution suggested by US 2004/0207385 is not applicable.

Furthermore, the arrangement suggested in US 2004/0207385 is not adapted for contact free and absolute position determination. As depicted in FIGS. 8 and 9 of US 2004/0207385 and the corresponding text in paragraphs 0053 and 0054 additional components such as force sensors or electrical resistors are required if absolute measurements are to be performed. Thus, it is a disadvantage of the arrangement suggested in 2004/0207385 that absolute measurements cannot be performed without the adding of contact requiring elements, such as force sensors and electrical resistors—the latter being implemented as a voltage divider.

It is an object of the present invention to provide a space saving assembly for measuring an absolute position, such as an absolute angular position, of a rotatably mounted member, such as a dose indicator barrel, in a medication delivery device.

SUMMARY OF THE INVENTION

The above-mentioned object is complied with by providing, in a first aspect, a medication delivery device comprising a position determining assembly for detecting absolute positions of a first member relative to a second member of the medication delivery device, the position determining assembly comprising a plurality of transmitter electrodes arranged on the first member, the plurality of transmitter electrodes being arranged along a substantially helical path, a plurality of receiver electrodes arranged on the first member, the plurality of receiver electrodes being arranged along a substantially helical path, wherein a number of transmitter electrodes form pairs of interconnected electrode elements with a number of receiver electrodes, and a reading assembly fixedly arranged relative to the second member, the reading assembly comprising a plurality of transmitters arranged to electrically couple to one or more receiver electrodes of the first member, and a plurality of receivers arranged to electrically couple to one or more transmitter electrodes of the first member.

The first member may comprise a rotatably mounted member, such as a rotatably mounted dose indication barrel, whereas the second member may form part of a housing of the medication delivery device. The rotatably mounted dose indicator barrel may be arranged to rotate about, and displace along, a centre axis of the medication delivery device, said centre axis also defining a centre axis of the housing of the medication delivery device.

Interconnected pairs of transmitter and receiver electrodes of the first member may be galvanically isolated from other interconnected pairs of transmitter and receiver electrodes. Thus, according to the present invention electrode elements of interconnected pairs of transmitter and receiver electrodes are provided along a substantially helical-shaped path.

Along the above-mentioned substantially helical-shaped path the transmitter electrodes may form a first periodic pattern. Similarly, the receiver electrodes may form a second periodic pattern along the substantially helical-shaped path. According to the present invention a periodicity of the first periodic pattern may be different from a periodicity of the second periodic pattern. Thus, according to the present invention the transmitter and receiver electrodes are spatially shifted along the substantially helical-shaped path. The total lengths of the first and second periodic patterns may be essentially the same and within the range 100-150 mm.

To ease access to the plurality of transmitter and receiver electrodes, said plurality of transmitter and receiver electrodes may be arranged on first and second exterior surface parts of the first member, respectively.

The first member may be adapted to perform a combined rotational and translational movement relative to the second member.

The electrical coupling between transmitters of the reading assembly and one or more receiver electrodes of the first member may comprise a capacitive coupling. In this situation, the electrodes forming the transmitters of the reading assembly and the one or more receiver electrodes of the first member may be implemented as capacitor plates. Also, the electrical coupling between receivers of the reading assembly and one or more transmitter electrodes of the first member may comprise a capacitive coupling between electrodes being formed as capacitor plates.

The reading assembly may comprise eight transmitters arranged in a row. The eight transmitters may be driven in pairs so that the same transmitter signal is provided to two parallel coupled transmitters. In a row of eight transmitters a first transmitter signal may be applied to the first and the fifth transmitter in the row, whereas a second transmitter signal may be applied to the second and the sixth transmitter in the row. Similarly, a third transmitter signal may be applied to the third and the seventh transmitter in the row, and a fourth transmitter signal may be applied to the fourth and the eighth transmitter in the row. The first, second, third and fourth transmitter signals may be phase shifted relative to each other—for example by an angle of around 90 degrees. The reading assembly may further comprise two receivers. Each receiver may be arranged as a number of triangular-shaped electrodes.

The transmitters and the receivers of the reading assembly may be arranged on a flexible carrier, such as on a flex print. By arranging the reading assembly on a flexible carrier the shape of the reading assembly can be adjusted to fit the shape of the housing of the medication delivery device and the shape of the first member.

The medication delivery device according to the first aspect of the present invention may further comprise an electronic control circuit for generating and handling electrical signals to and from the transmitters and the receivers of the reading assembly, respectively.

As already mentioned, the first member may be a movably mounted member, such as a rotatably mounted dose indicator barrel positioned within the medication delivery device.

In a second aspect, the present invention relates to a method for determining absolute positions of a first member relative to a second member of a medication delivery device, the method comprising the steps of
　providing a plurality of transmitter electrodes arranged on the first member, the plurality of transmitter electrodes being arranged along a substantially helical path,
　providing a plurality of receiver electrodes arranged on the first member, the plurality of receiver electrodes being arranged along a substantially helical path, wherein a number of transmitter electrodes form pairs of interconnected electrode elements with a number of receiver electrodes,
　providing a reading assembly fixedly arranged relative to the second member, the reading assembly comprising a plurality of transmitters arranged to electrically couple to one or more receiver electrodes of the first member, and a plurality of receivers arranged to electrically couple to one or more transmitter electrodes of the first member, and
　providing first, second, third and fourth transmitter signals to respective ones of first, second, third and fourth transmitters of the reading assembly, the first, second, third and fourth transmitter signals being mutually shifted in phase.

According to the method of the second aspect of the present invention, the first member may comprise a rotatably mounted member, such as a rotatably mounted dose indicator barrel, whereas the second member forms part of a housing of the medication delivery device. The rotatably mounted dose indicator barrel may be arranged to rotate about, and displace along, a centre axis of the medication delivery device, said centre axis also defining a centre axis of the housing of the medication delivery device.

A previously mentioned, the first, second, third and fourth transmitter signals may be approximately 90 degrees out of phase. The transmitter signals may be sinusoidal or PWM-generated signals having a fundamental frequency in the 1-100 kHz range. However, transmitter signals having a fundamental frequency of around 10 kHz are preferable, especially if the transmitter signals are generated by PWM. The reason for this being that a 10 MHz signal is required in order to generate a suitable 10 kHz signal. In addition, the frequency of the transmitter signals is kept in the low end in order to reduce the influence of parasitic capacitances. Amplitude levels in the 1-5 V range, such as 1.5-3 V, may be applicable.

The first, second, third and fourth transmitter signals may be provided to respective pairs of transmitters. Thus, of a row comprising eight transmitters the first transmitter signal may be applied to a first and a fifth transmitter, whereas the second transmitter signal may be applied to a second and a sixth transmitter. Similarly, the third transmitter signal may be applied to a third and a seventh transmitter, whereas the fourth transmitter signal may be applied to a fourth and an eighth transmitter in the row.

The electrical coupling between transmitters of the reading assembly and one or more receiver electrodes of the first member may comprise a capacitive coupling. Similarly, the electrical coupling between receivers of the reading assembly and one or more transmitter electrodes of the first member may comprise a capacitive coupling.

As previously mentioned, interconnected pairs of transmitter and receiver electrodes of the first member may be galvanically isolated from other interconnected pairs of transmitter and receiver electrodes. Thus, electrode elements of interconnected pairs of transmitter and receiver electrodes are provided along a substantially helical-shaped path.

Along the above-mentioned substantially helical-shaped path the transmitter electrodes may form a first periodic pattern. Similarly, the receiver electrodes may form a second periodic pattern along the substantially helical-shaped path. According to the present invention a periodicity of the first periodic pattern may be different from a periodicity of the second periodic pattern. Thus, according to the present invention the transmitter and receiver electrodes are spatially shifted along the substantially helical-shaped path. The total lengths of the first and second periodic patterns may be essentially the same and within the range 100-150 mm.

To ease access to the plurality of transmitter and receiver electrodes, said plurality of transmitter and receiver electrodes may be arranged on first and second exterior surface parts of the first member, respectively.

In a third aspect, the present invention relates to a medication delivery device comprising a position determining assembly for detecting absolute positions of a first member relative to a second member of the medication delivery device, the position determining assembly comprising coupling means adapted to receive and re-transmit an electrical signal coupled to said coupling means, said coupling means forming a substantially helical path on the first member, transmitting means adapted to electrically couple one or more transmitter signals to the coupling means of the first member, said transmitting means being fixedly arranged relative to the second member, receiving means adapted to receive re-transmitted electrical signals from the coupling means of the first member, said receiving means being fixedly arranged relative to the second member, and electronic control means adapted to generate suitable transmitter signals, and to process receiver signals from the receiving means in order to determine an absolute position of the first member relative to the second member.

The coupling means of the first member may comprise a plurality of transmitter electrodes arranged on said first member, the plurality of transmitter electrodes being arranged along a substantially helical path. Furthermore, the coupling means may comprise a plurality of receiver electrodes arranged on said first member, the plurality of receiver electrodes being arranged along a substantially helical path. A number of transmitter electrodes may form pairs of interconnected electrode elements with a number of receiver electrodes.

The transmitting and receiving means may be incorporated into a reading assembly fixedly arranged relative to the second member. The reading assembly may comprise a plurality of transmitters arranged to electrically couple to one or more receiver electrodes of the first member, and a plurality of receivers arranged to electrically couple to one or more transmitter electrodes of the first member.

The first member may comprise a rotatably mounted member, such as a rotatably mounted dose indication barrel, whereas the second member may form part of a housing of the medication delivery device. The rotatably mounted dose indicator barrel may be arranged to rotate about, and displace along, a centre axis of the medication delivery device, said centre axis also defining a centre axis of the housing of the medication delivery device.

Further implementations of the reading assembly, the transmitter and receiver electrodes, the transmitter signals etc. may be as described in connection with the first and second aspects of the present invention.

BRIEF DESCRIPTION OF THE DRAWINGS

The present invention will now be explained with reference to the accompanying drawings, wherein.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE INVENTION

In its broadest aspect the present invention relates to a medication delivery device comprising an assembly for determining the absolute position of a first member, such as a rotatably mounted dose indicator barrel, relative to a second member, such as a housing part of the medication delivery device. The assembly is implemented with the aim to take up minimum space within the medication delivery device.

The above-mentioned requirements are provided for by providing, in one embodiment of the present invention, an assembly comprising a reading assembly having eight transmitters arranged in a row. The eight transmitters are operated in pairs so that two transmitters are provided with the same transmitter signal. The transmitter signals provided to the four pairs of transmitters are phase shifted 90 degrees.

Figure 1:
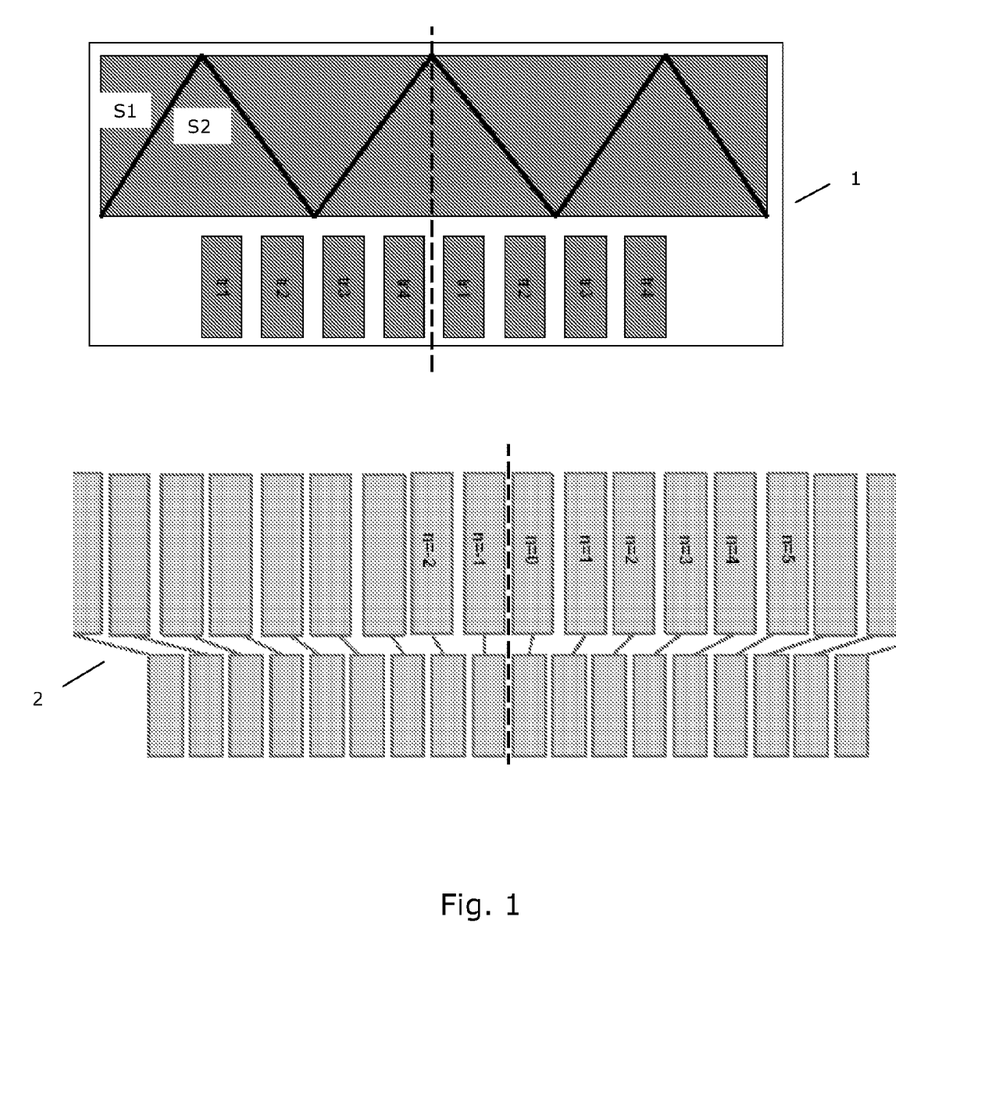
FIG. 1 shows a reading assembly comprising two receivers and eight transmitters, and an associated scale comprising transmitter and receiver electrodes.

An assembly according to the above-mentioned embodiment of the present invention is depicted in FIG. 1 where the transmitters are denoted tr1-tr4. In the assembly depicted in FIG. 1 a first transmitter signal is applied to both tr1-transmitters. Similarly, a phase shifted second transmitter signal is applied to both tr2-transmitters. This second transmitter signal is phase shifted 90 degrees relative to the transmitter signal provided to the two tr1-transmitters. A phase shifted third transmitter signal is provided to the two tr3-transmitters, and finally, a phase shifted fourth transmitter signal is provided to the two tr4-transmitters. In FIG. 1 S1 and S2 are two receivers.

The number of transmitters may differ from the above-mentioned eight. Thus, a number of twelve transmitters may be operated in pairs by applying six phase shifted transmitter signals. Such six phase shifted transmitters signals will be phase shifted 60 degrees.

Figure 3:
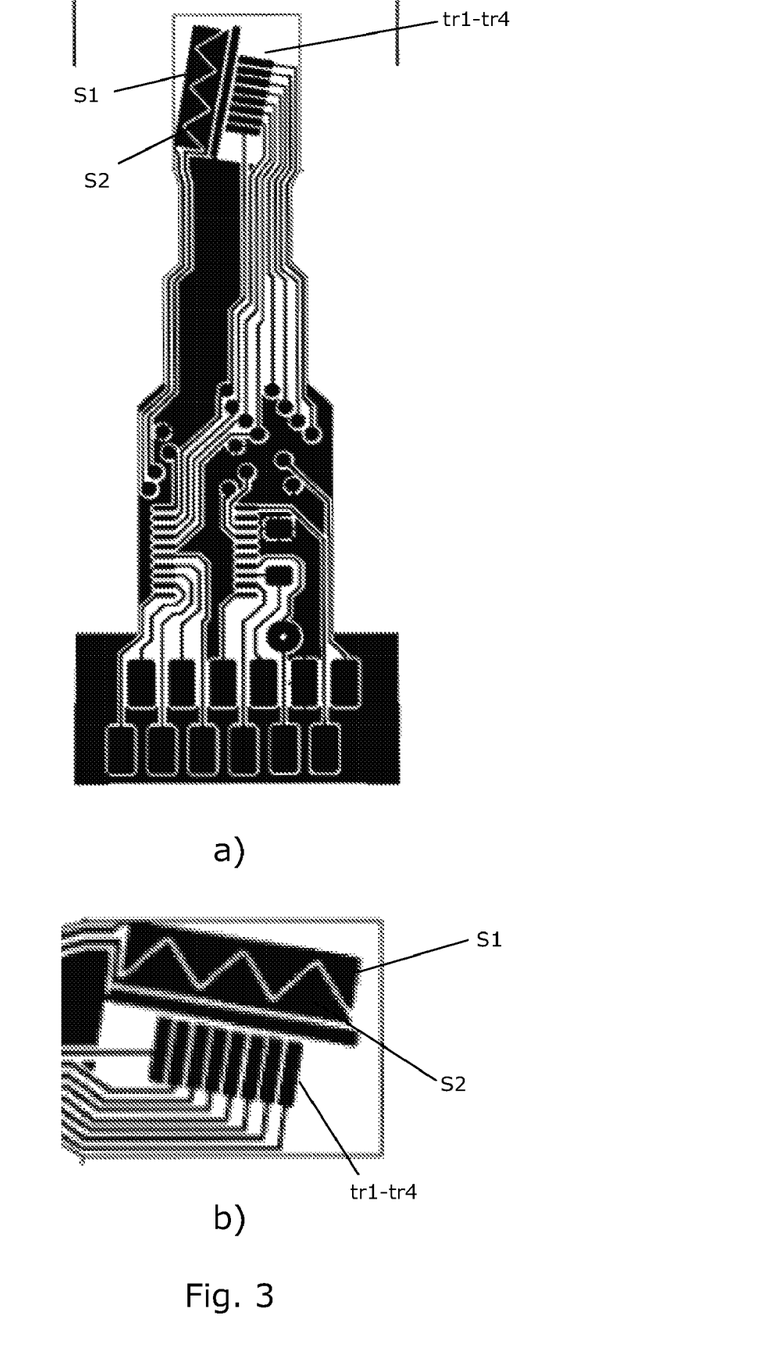
FIG. 3 shows a print layout.
Figure 5:
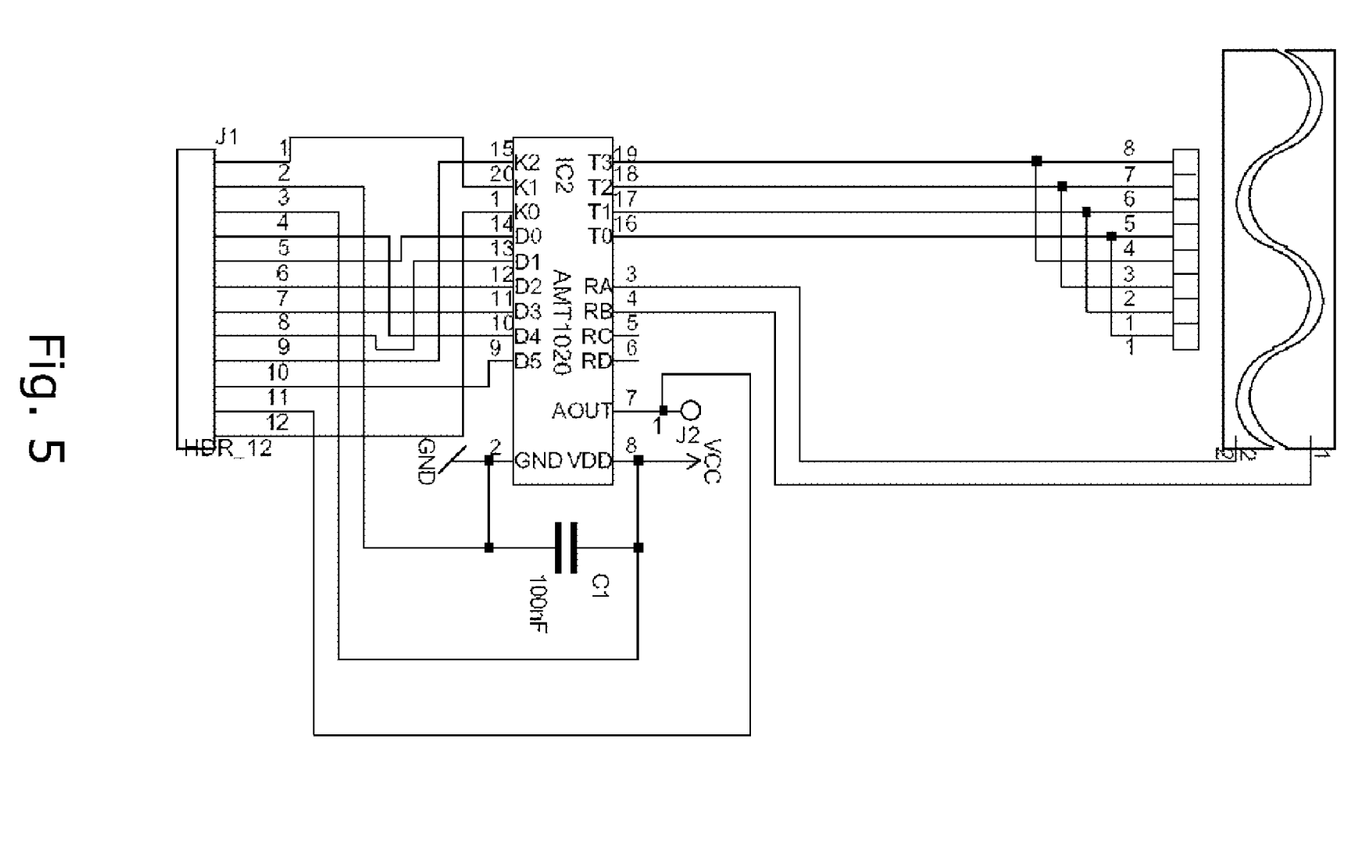
FIG. 5 shows a control circuit capable of generating four transmitter signals and handling signals from two receivers.

The physical implementation of the transmitters tr1-tr4 and receivers S1, S2 are depicted in FIG. 3b where the transmitters and receivers are arranged a flexible PCB, such as on a flex print. As shown in FIG. 3a the transmitters and receivers are implemented on the same PCB as the electronic control circuit capable of generating the required four phase shifted transmitter signals and handling/processing signals from the receivers. The electronic control circuit itself is shown in FIG. 5.

The detection principle associated with the assembly depicted in FIG. 1 is normally referred to as the displaced trace method. As seen, the reading assembly 1 consists of two main parts—a scale 2 (placed on an exterior surface part of for example a rotatably mounted dose indicator barrel or on another movable part) having two rows of rectangular electrodes (numbered n=−N, −N+1, . . . , −2, −1, 0, 1, 2, . . . , N), and the reading head (fixedly positioned relative to the housing of the medication delivery device) with generator/transmitter electrodes tr1-tr4 and the receiver electrodes S1-S2.

Figure 2:
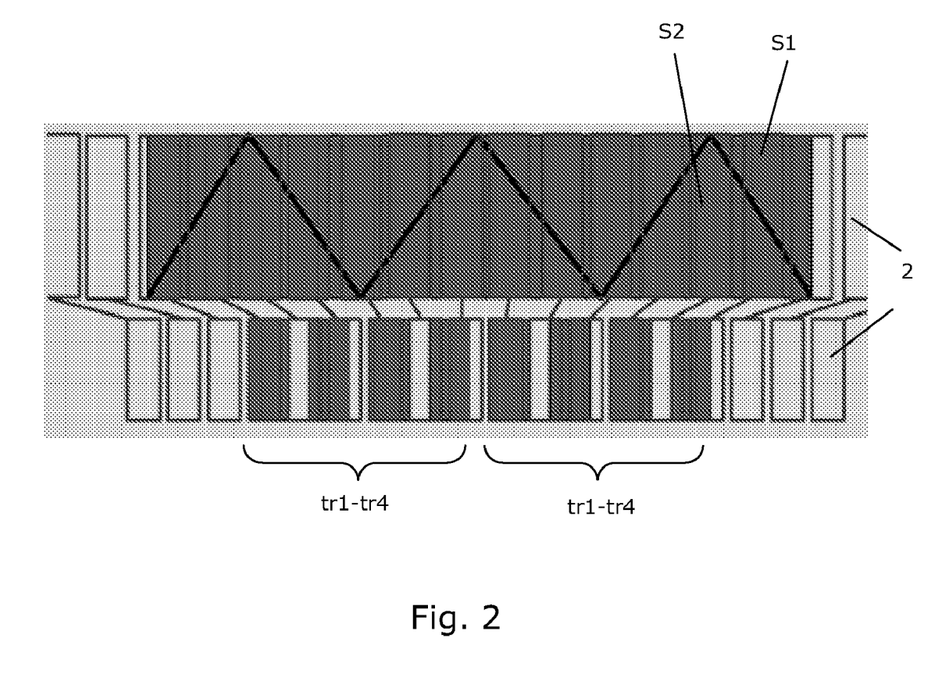
FIG. 2 shows a reading assembly comprising two receivers and eight transmitters, and an associated scale comprising transmitter and receiver electrodes, where the transmitter electrodes are aligned with the receivers of the reading assembly and where the receiver electrodes are aligned with the transmitters of the reading assembly.

Still referring to FIG. 1 the centre-to-centre distance between neighbouring electrodes of the upper row is larger than the centre-to-centre distance between neighbouring electrodes of the lower row, As seen in FIG. 1 each electrode of the upper row is electrically connected with an electrode of the lower row thereby forming an electrode element. As seen, the electrode elements are galvanically isolated from each other. When the scale of electrode elements is placed over or aligned with the reading assembly 1 (see FIG. 2), the signal from the transmitters tr1-tr4 is coupled to the receiver electrodes S1, S2 via the two rows of electrodes forming the scale. Thus, transmitter signals provided to transmitters tr1-tr4 are electrically coupled to electrodes of the lower row (receiver electrodes) of the scale 2, and re-transmitted from the upper electrodes (transmitter electrodes) of the scale 2 to be received by receivers S1, S2. Preferably, the electrical couplings between transmitters tr1-tr4 and receiver electrodes, and between the transmitter electrodes and receivers S1, S2 are capacitive.

The centre of the reading assembly (transmitters and receivers) and the scale is in FIG. 1 indicated by a dashed line. Thus, both the reading assembly and the scale are symmetric around this dashed line. Off-centre the two rows of electrodes forming the scale are displaced whereas in the centre of the scale (at the dashed line) the two rows of electrodes are aligned. This arrangement of the electrodes influences the received signal in such a way that the phase of the signals from the two receiver electrodes S1, S2 are changing along the scale. In this way is it possible two perform an absolute measurement of the position of the reading assembly relative to the scale.

In the medication delivery device the space for the reading assembly is rather limited—the maximum length (along the scale direction) is 8.25 mm whereas the maximum allowable height is 6 mm. With this limited space available a configuration comprising two groups of four transmitters tr1-tr4 are preferred. Each of the four transmitters tr1-tr4 transmits a sinusoidal-like transmitter signal and, as previously mentioned, the transmitters tr1-tr4 are driven out of phase. Thus, the transmitter signal provided to transmitter tr2 is phase shifted 90 degrees relative to tr1, the transmitter signal provided to transmitter tr3 is phase shifted 180 degrees relative to tr1 and, finally, the transmitter signal provided to transmitter tr3 is phase shifted 270 degrees relative to tr1.

By using two sets of transmitters tr1-tr4 two wavelengths of the transmitter signal are used along the scale length in the reading head. With two wavelengths of transmitters two wavelengths of receivers are available.

The maximum allowable displacement between the two electrode rows of the scale is given by the fact that the maximum phase difference between the signals from receivers S1 and 52 is ±180°. This corresponds to a maximum displacement of ±½ wavelength of the transmitters. This maximum displacement of ±½ wavelength of the transmitters increases the length of the receiver from two to three wavelengths (two wavelengths+½ wavelength at each end of the scale).

A maximum allowable total length of 8.25 mm distributed over 3 wavelengths result in a receiver wavelength of 2.75 mm. The length of curvature along a typical dose indicator barrel scale is 114 mm. However, this measure only applies for the centre point of the reading assembly. To compensate for this the length of the scale has to be increased with a length that corresponds to the length of the receivers. This gives a total scale length of 122.25 mm. Thus, the distance from the centre point of the scale to both ends of the scale is 61.13 mm.

At the ends of the scale the displacement is ½ wavelength. Thus, the displacement factor is given by ½ wavelength divided by the half scale length causing the distance between the electrodes aligned with the receiver electrodes in the reading head to be 2.2% higher than the distance between the electrodes aligned with the transmitter electrodes in the reading head.

A maximum allowable length of 8.25 mm spilt over 3 wavelengths combined with a displacement factor of 2.2% gives a transmitter wavelength of 2.68 mm. Thus, the centre-to-centre distance between the transmitters is 0.66 mm.

Figure 4:
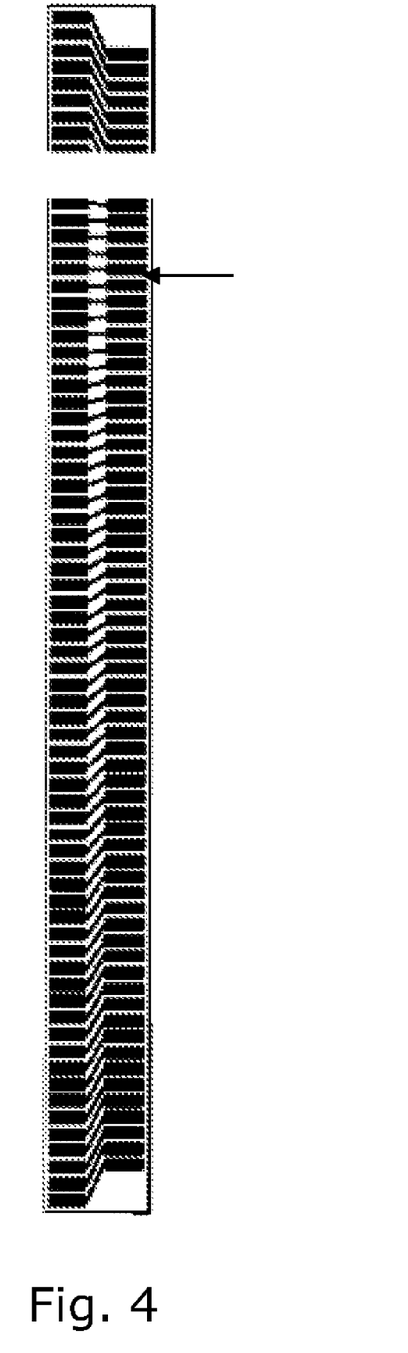
FIG. 4 shows a scale comprising spatially displaced transmitter and receiver electrodes.

One half of the scale is shown in FIG. 4—the centre of the scale is at the position of the arrow. As seen, the displacement of the electrodes in the two rows increases in the direction of the end of the scale. It should be noted that the scale depicted in FIG. 4, when arranged on a rotatably mounted dose indicator barrel, will take a substantially helical shape in that the scale is preferably arranged on a substantially cylindrically shaped outer surface of the rotatably mounted dose indicator barrel. Furthermore, since the rotatably mounted dose indicator barrel should be allowed to rotate more than one revolution the scale will unavoidable form a substantially helical shape.

Figure 6:
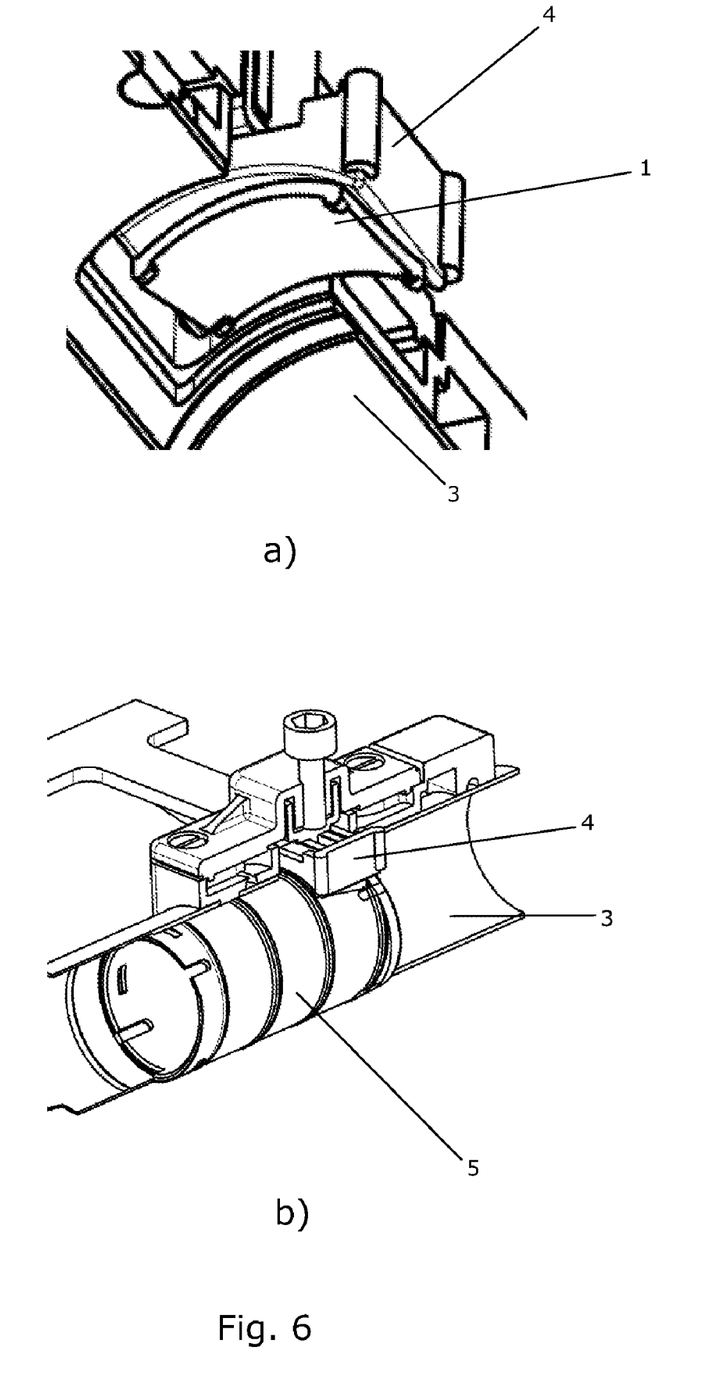
FIG. 6 shows the positioning determining assembly according to the present invention mounted in a medication delivery device.

In FIG. 6 the position determining assembly according to the present invention is depicted. FIG. 6 shows a housing 3 of a medication delivery device and an assembly holder 4 for holding the reading assembly 1 according to the present invention. As previously mentioned, the reading assembly 1 comprises eight transmitters (not shown) and two receivers (not shown). The reading assembly is implemented as depicted in the upper part of FIG. 1.

The reading assembly 1 is positioned on assembly holder 4 which can be displaced along a radial direction of the medication delivery device. In this way the reading assembly 1 can be brought into the vicinity of the exterior surface of a dose indicator barrel 5 upon which the scale (see FIG. 4) is arranged. Thus, then the dose indicator barrel is rotated it performs a combined rotational/translational movement in relation to the housing of the medication delivery device. This combined rotational/translational movement of the dose indicator barrel 5 causes the scale (see FIG. 4) to pass through the transmitters and the receivers of the reading assembly. Via a capacitive coupling the transmitters and the receivers, via the electrodes on the dose indicator barrel, an absolute position of the dose indicator barrel is determinable.

The invention claimed is:

1. A medication delivery device comprising:
   a position determining assembly for detecting absolute positions of a first member relative to a second member of the medication delivery device, the position determining assembly comprising:
      a plurality of transmitter electrodes arranged on the first member, the plurality of transmitter electrodes being arranged along a substantially helical path,
      a plurality of receiver electrodes arranged on the first member, the plurality of receiver electrodes being arranged along a substantially helical path, wherein a number of transmitter electrodes form pairs of interconnected electrode elements with a number of receiver electrodes, and
      a reading assembly fixedly arranged relative to the second member, the reading assembly comprising a plurality of transmitters arranged to electrically couple to one or more receiver electrodes of the first member, and a plurality of receivers arranged to electrically couple to one or more transmitter electrodes of the first member.

2. A medication delivery device according to claim 1, wherein the first member comprises a rotatably mounted member, and wherein second member forms part of a housing of the medication delivery device.

3. A medication delivery device according to claim 1, wherein interconnected pairs of transmitter and receiver electrodes are galvanically isolated from other interconnected pairs of transmitter and receiver electrodes.

4. A medication delivery device according to claim 1, wherein the transmitter electrodes form a first periodic pattern along the helical path.

5. A medication delivery device according to claim 1, wherein the receiver electrodes form a second periodic pattern along the helical path, wherein a periodicity of the first periodic pattern is different from a periodicity of the second periodic pattern.

6. A medication delivery device according to claim 1, wherein the plurality of transmitter and receiver electrodes are arranged on first and second exterior surface parts of the first member, respectively.

7. A medication delivery device according to claim 1, wherein the first member is adapted to perform a combined rotational and translational movement relative to the second member.

8. A medication delivery device according to claim 1, wherein the electrical coupling between transmitters of the reading assembly and receiver electrodes of the first member comprises a capacitive coupling.

9. A medication delivery device according to claim 1, wherein the electrical coupling between receivers of the reading assembly and transmitter electrodes of the first member comprises a capacitive coupling.

10. A medication delivery device according to claim 1, wherein the reading assembly comprises eight transmitters.

11. A medication delivery device according to claim 1, wherein the reading assembly comprises two receivers.

12. A medication delivery device according to claim 1, wherein the transmitters and the receivers of the reading assembly are arranged on a flexible carrier, such as a flex print.

13. A medication delivery device according to claim 1, further comprising an electronic control circuit for generating and handling electrical signals to and from the transmitters and the receivers of the reading assembly, respectively.

14. A medication delivery device according to claim 1, wherein the first member comprises a rotatably mounted dose indicator barrel.

15. A method for determining absolute positions of a first member relative to a second member of a medication delivery device, the method comprising:
   providing a plurality of transmitter electrodes arranged on the first member, the plurality of transmitter electrodes being arranged along a substantially helical path,
   providing a plurality of receiver electrodes arranged on the first member, the plurality of receiver electrodes being arranged along a substantially helical path, wherein a number of transmitter electrodes form pairs of interconnected electrode elements with a number of receiver electrodes,
   providing a reading assembly fixedly arranged relative to the second member, the reading assembly comprising a plurality of transmitters arranged to electrically couple to one or more receiver electrodes of the first member, and a plurality of receivers arranged to electrically couple to one or more transmitter electrodes of the first member, and
   providing first, second, third and fourth transmitter signals to respective ones of first, second, third and fourth transmitters of the reading assembly, the first, second, third and fourth transmitter signals being mutually shifted in phase.

16. A method according to claim 15, wherein the first member comprises a rotatably mounted member, and wherein second member forms part of a housing of the medication delivery device.

17. A method according to claim 15, wherein the first, second, third and fourth transmitter signals are approximately 90 degrees out of phase.

18. A method according to claim 15, wherein the electrical coupling between transmitters of the reading assembly and one or more receiver electrodes of the first member comprises a capacitive coupling.

19. A method according to claim 15, wherein the electrical coupling between receivers of the reading assembly and one or more transmitter electrodes of the first member comprises a capacitive coupling.

20. A method according to claim 15, wherein interconnected pairs of transmitter and receiver electrodes are galvanically isolated from other interconnected pairs of transmitter and receiver electrodes.

21. A method according to claim 15, wherein the transmitter electrodes form a first periodic pattern along the helical path.

22. A method according to claim 21, wherein the receiver electrodes form a second periodic pattern along the helical path, wherein a periodicity of the first periodic pattern is different from a periodicity of the second periodic pattern.

23. A method according to claim 15, wherein the plurality of transmitter and receiver electrodes are arranged on first and second exterior surface parts of the first member, respectively.

24. A method according to claim 15, wherein the first member is adapted to perform a combined rotational and translational movement relative to the second member.

25. A method according to claim 15, wherein the first member comprises a rotatably mounted dose indicator barrel.

* * * * *